United States Patent
Carter et al.

(10) Patent No.: US 10,166,389 B2
(45) Date of Patent: Jan. 1, 2019

(54) SINGLE-WIRE ELECTRODE ARRAY

(71) Applicant: Cochlear Limited, Macquarie University, NSW (AU)

(72) Inventors: Paul Michael Carter, West Pennant Hills (AU); Torsten Lehmann, Earlwood (AU)

(73) Assignee: Cochlear Limited, Macquarie University (AU)

(*) Notice: Subject to any disclaimer, the term of this patent is extended or adjusted under 35 U.S.C. 154(b) by 0 days.

(21) Appl. No.: 15/263,574

(22) Filed: Sep. 13, 2016

(65) Prior Publication Data

US 2018/0071532 A1    Mar. 15, 2018

(51) Int. Cl.
| | | |
|---|---|---|
| A61N 1/00 | (2006.01) | |
| A61N 1/36 | (2006.01) | |
| A61N 1/05 | (2006.01) | |

(52) U.S. Cl.
CPC ....... *A61N 1/36032* (2013.01); *A61N 1/0541* (2013.01); *A61N 1/36038* (2017.08)

(58) Field of Classification Search
CPC .......................... A61N 1/0541; A61N 1/36032
See application file for complete search history.

(56) References Cited

U.S. PATENT DOCUMENTS

| | | | |
|---|---|---|---|
| 6,418,348 B1 | 7/2002 | Witte | |
| 6,826,430 B2 | 11/2004 | Faltys et al. | |
| 8,082,040 B2 | 12/2011 | Ibrahim et al. | |
| 8,116,876 B2 | 2/2012 | Stypulkowski | |
| 8,433,402 B2 | 4/2013 | Ruben et al. | |
| 2004/0193021 A1* | 9/2004 | Zdeblick | A61B 5/036 600/300 |
| 2009/0005836 A1* | 1/2009 | Chang | A61N 1/0541 607/57 |
| 2010/0030298 A1* | 2/2010 | Martens | A61N 1/0529 607/45 |
| 2010/0280366 A1* | 11/2010 | Arne | A61B 5/046 600/425 |
| 2011/0264182 A1 | 10/2011 | Cowley | |
| 2012/0161945 A1 | 6/2012 | Single et al. | |
| 2013/0268043 A1 | 10/2013 | Tasche et al. | |
| 2014/0163662 A1 | 6/2014 | Beerling et al. | |
| 2016/0015975 A1 | 1/2016 | Dueck et al. | |

FOREIGN PATENT DOCUMENTS

KR     20090047498 A     5/2009

OTHER PUBLICATIONS

International Search Report and Written Opinion in corresponding International Application No. PCT/IB2017/055391, dated Dec. 27, 2017, 13 pages.

* cited by examiner

*Primary Examiner* — Mallika D Fairchild
(74) *Attorney, Agent, or Firm* — Edell, Shapiro & Finnan, LLC

(57) ABSTRACT

Tissue-stimulating prostheses that include a single-wire electrode array for delivery of electrical stimulation signals (current stimulation) to a recipient. The single-wire electrode array comprises a plurality of electrode devices that are all connected to a stimulator unit via a single-wire connection (i.e., only one wire or lead). Each of the plurality of electrode devices is individually addressable by the stimulator unit for delivery of the current signals to the recipient via the single-wire connection.

20 Claims, 10 Drawing Sheets

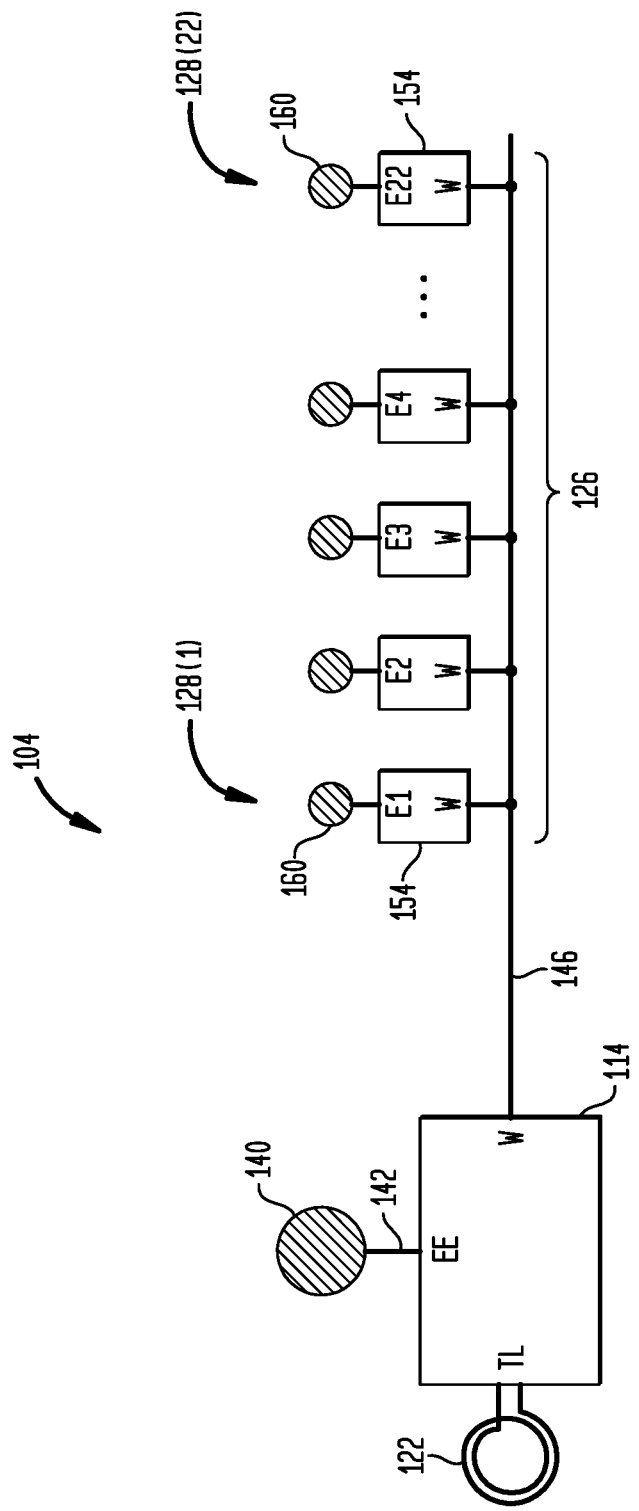

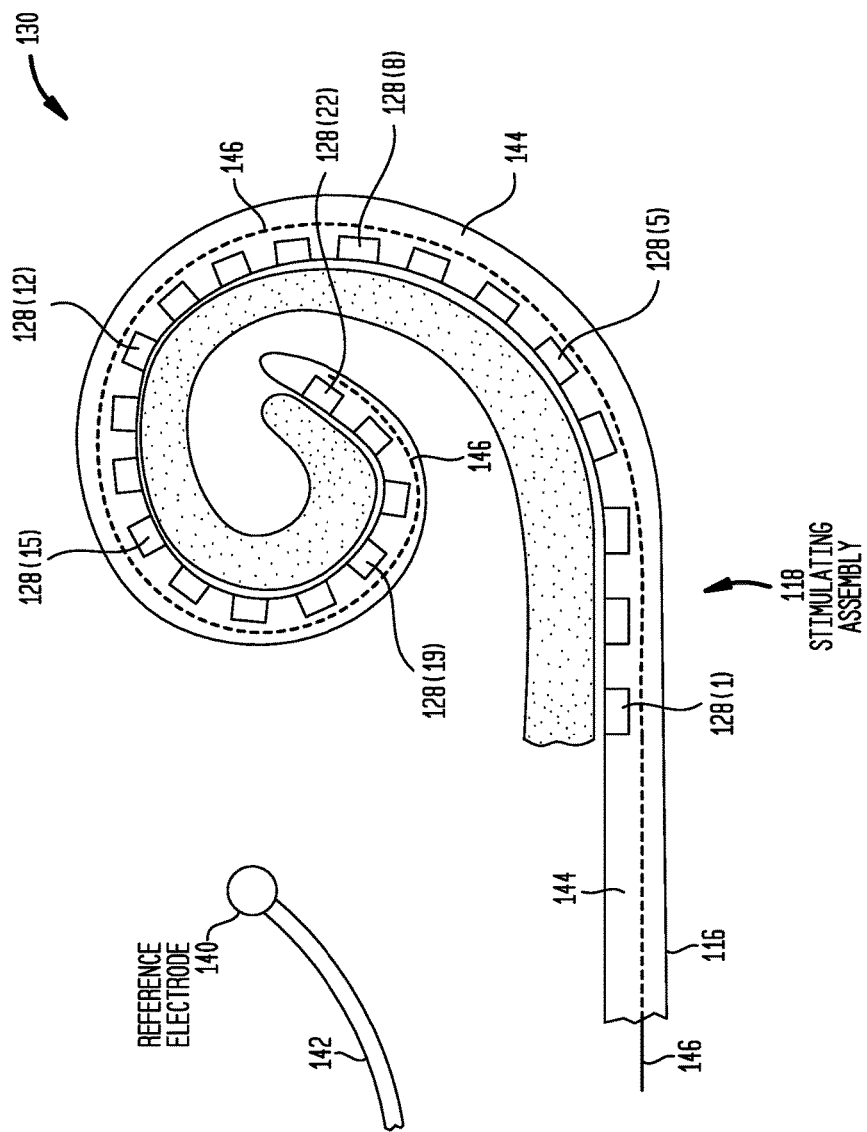

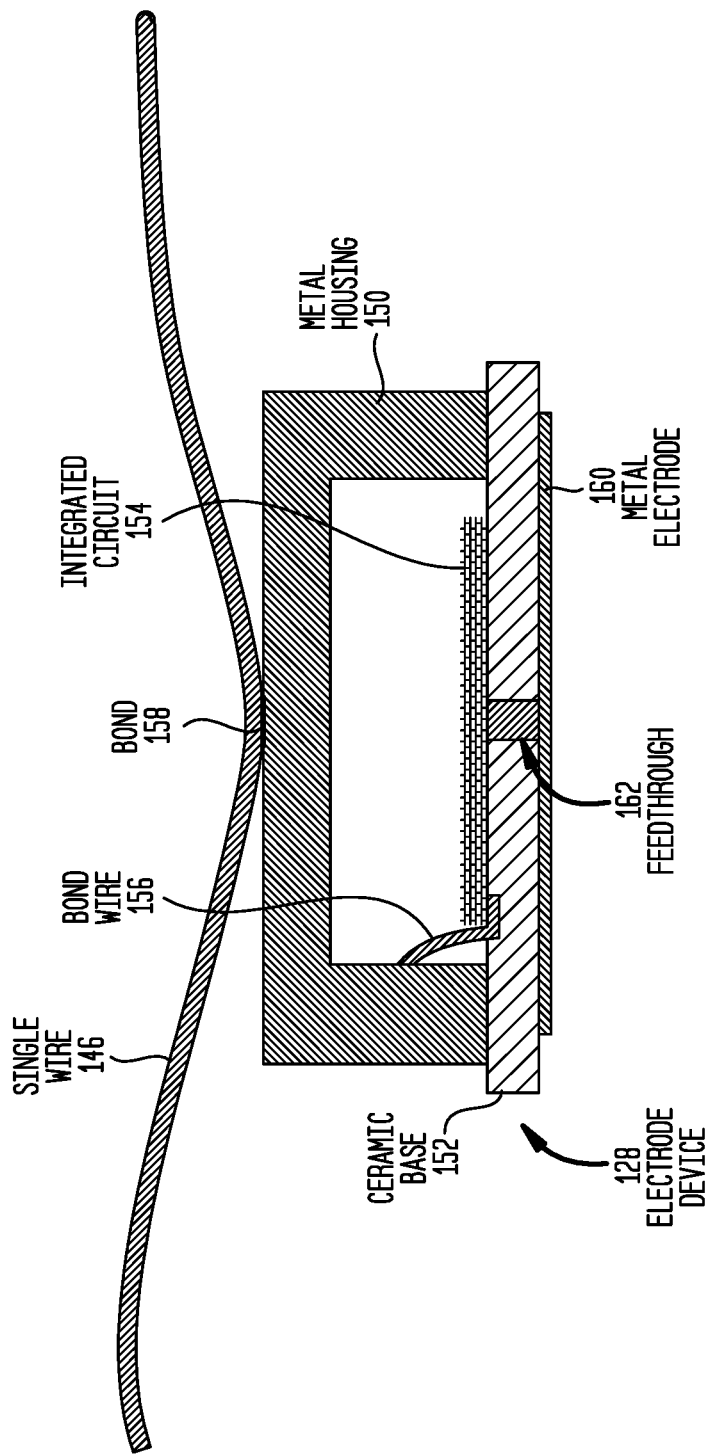

SINGLE-WIRE ELECTRODE ARRAY

BACKGROUND

Field of the Invention

The present invention relates generally to tissue-stimulating prostheses.

Related Art

There are several types of medical devices that operate by delivering electrical (current) stimulation to the nerves, muscle or other tissue fibers of a recipient. These medical devices, referred to herein as tissue-stimulating prostheses, typically deliver current stimulation to compensate for a deficiency in the recipient. For example, tissue-stimulating hearing prostheses, such as cochlear implants, are often proposed when a recipient experiences sensorineural hearing loss due to the absence or destruction of the cochlear hair cells, which transduce acoustic signals into nerve impulses. Auditory brainstem stimulators are another type of tissue-stimulating hearing prostheses that might be proposed when a recipient experiences sensorineural hearing loss due to damage to the auditory nerve.

SUMMARY

In one aspect presented herein, a tissue-stimulating prosthesis system is provided. The tissue-stimulating prosthesis system comprises: a stimulator unit configured to generate, based on at least one of the one or more processed signals, current signals for delivery to a recipient; and a single-wire electrode array comprising a plurality of electrode devices all connected to the stimulator unit via a single wire connection, wherein the plurality of electrode devices are individually addressable by the stimulator unit via the single wire connection for delivery of the current signals to the recipient.

In another aspect presented herein, a tissue-stimulating prosthesis system is provided. The tissue-stimulating prosthesis system comprises: a plurality of electrode devices implanted in a recipient; an implantable power supply; a stimulator unit configured to generate current signals for delivery to the recipient; and only a single wire connection electrically connecting all of the electrode devices to the stimulator unit.

In another aspect presented herein, a method is provided. The method comprises: at a stimulator unit of a tissue-stimulating prosthesis system implantable in a recipient, generating electrical stimulation signals; and delivering the electrical stimulation signals to a recipient of the tissue-stimulating prosthesis system via a single-wire electrode array comprising a plurality of electrode devices all connected to the stimulator unit via a single wire connection.

BRIEF DESCRIPTION OF THE DRAWINGS

Embodiments of the present invention are described herein in conjunction with the accompanying drawings, in which:

FIG. 1B is a schematic block diagram illustrating further details of a cochlear implant system in accordance with embodiments presented herein;

FIG. 1C is a schematic diagram illustrating a stimulating assembly that includes a single-wire electrode array in accordance with embodiments presented herein;

FIG. 2 is schematic diagram illustrating an electrode device in accordance with embodiments presented herein.

DETAILED DESCRIPTION

Presented herein are tissue-stimulating prostheses that include a single-wire electrode array for delivery of electrical stimulation signals (current stimulation) to a recipient. The single-wire electrode array comprises a plurality of electrode devices that are all connected to a stimulator unit via a single-wire connection (i.e., only one wire or lead). Each of the plurality of electrode devices is individually addressable by the stimulator unit for delivery of the current signals to the recipient via the single-wire connection.

As noted, there are several types of tissue-stimulating prostheses that deliver stimulation to compensate for a deficiency in a recipient. Merely for ease of illustration, the embodiments presented herein are primarily described herein with reference to one type of tissue-stimulating prosthesis, namely a cochlear implant. It is to be appreciated that the techniques presented herein may be used with other tissue-stimulating prostheses including, for example, auditory brainstem stimulators, implantable pacemakers, defibrillators, functional electrical stimulation devices, pain relief stimulators, visual prostheses, other neural or neuro-muscular stimulators, etc.

Figure 1A:
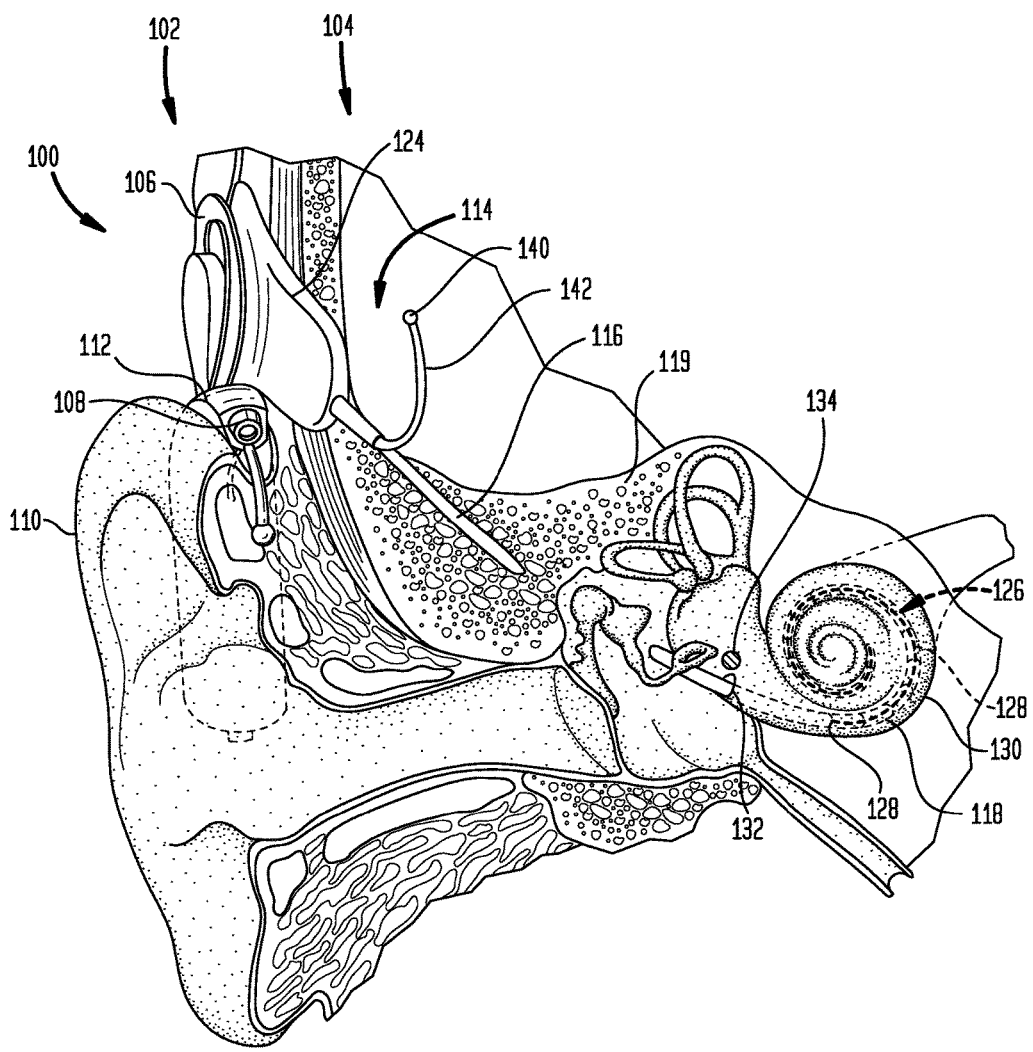
FIG. 1A is a schematic diagram illustrating a cochlear implant system comprising a single-wire electrode array in accordance with embodiments presented herein.

FIG. 1A is schematic diagram of an exemplary cochlear implant system 100 configured to implement embodiments of the present invention. The cochlear implant system 100 comprises an external component 102 and an internal/implantable component 104. In this example, the implantable component 104 is a cochlear implant.

The external component 102 is directly or indirectly attached to the body of the recipient and typically comprises an external coil 106 and, generally, a magnet (not shown in FIG. 1A) fixed relative to the external coil 106. The external component 102 also comprises one or more sound input elements 108 (e.g., microphones, telecoils, etc.) for detecting/receiving sound signals, and a sound processing unit 112. The sound processing unit 112 includes, for example, a power source (not shown in FIG. 1A) and a sound processor (also not shown in FIG. 1A). The sound processor is configured to process electrical signals generated by a sound input element 108 that is positioned, in the depicted embodiment, by auricle 110 of the recipient. The sound processor provides the processed signals to external coil 106 via, for example, a cable (not shown in FIG. 1A).

The cochlear implant 104 comprises an implantable main module (implant body) 114, a lead region 116, and an elongate intra-cochlear stimulating assembly 118. The main module 114 comprises a stimulator unit 120 and an internal receiver/transceiver unit 124, sometimes referred to herein as transceiver unit 124. The transceiver unit 124 is connected to an implantable coil (FIG. 1B) and, generally, a magnet (not shown) is fixed relative to the internal coil 122.

The magnets in the external component 102 and cochlear implant 104 facilitate the operational alignment of the external coil 106 with the implantable coil 122. The operational alignment of the coils enables the implantable coil 122 to receive power and data from, and possibly send data to, the external coil 106. More specifically, in certain examples, external coil 106 transmits electrical signals (e.g., power and stimulation data) to implantable coil 122 via a closely-coupled link. Implantable coil 122 is typically a wire antenna coil comprised of multiple turns of electrically insulated single-strand or multi-strand platinum or gold wire. The electrical insulation of implantable coil 122 is provided by a flexible molding (e.g., silicone molding). In use, transceiver unit 124 may be positioned in a recess of the temporal bone of the recipient. Various other types of transfer methods, such as infrared (IR), electromagnetic, capacitive transfer, inductive transfer, etc. may be used to transfer the power from an external device to a cochlear implant and to transfer data between an external device and a cochlear implant. As such, FIG. 1A illustrates only one example arrangement Elongate stimulating assembly 118 is configured to be at least partially implanted in cochlea 130 and includes a plurality of longitudinally spaced intra-cochlear electrode devices 128. Stimulating assembly 118 extends through an opening in the cochlea 130 (e.g., cochleostomy 132, the round window 134, etc.) and has a proximal end connected to stimulator unit 120 via lead region 116 that extends through mastoid bone 119. As described further below, a single-wire connection, sometimes referred to herein more simply as a "single wire," is connected to all of electrode devices 128, and extends through the lead region 116 to the stimulator unit 120. In other words, all of the electrode devices 128 are connected to the stimulator unit 120 via the same single-wire connection.

Also shown in FIG. 1A is a reference electrode 140. Since the reference electrode 140 is positioned outside of the recipient's cochlea, the reference electrode is sometimes referred to as an extra-cochlear electrode (ECE). A reference lead region 142, which comprises a wire or lead embedded in an electrically-insulating material, electrically connects the reference electrode 140 to the stimulator unit 120. As described further below, the reference electrode 140 may, in certain arrangements, operate as a counter electrode when delivering stimulation current via one or more of the electrode devices 128.

FIG. 1B is a block diagram illustrating components of the cochlear implant 104, while FIG. 1C is a schematic diagram providing a more detailed view of the stimulating assembly 118 of FIG. 1A when implanted in cochlea 130. FIGS. 1B and 1C illustrate a specific arrangement in which stimulating assembly 118 comprises twenty-two (22) electrode devices 128, labeled in FIG. 1B as electrode devices 128(1) through 128(22). However, it is to be appreciated that embodiments presented herein may be implemented in alternative arrangements having different numbers of electrode devices.

As shown, electrode device 128(1) is the most basal/proximal electrode device, while electrode device 128(22) is the most distal/apical electrode device. The electrode devices 128(1)-128(22) are each disposed in an electrically-insulating body 144 formed, for example, from an elastomer or other resiliently flexible material. The electrode devices 128(1)-128(22) are all connected to a single-wire connection (i.e., a single wire or lead) 146, sometimes referred to herein as "single-wire" 146, that extends through the body 144 of the stimulating assembly 118 and the lead region 116 (not shown in FIG. 1B or 1C) to the stimulator unit 120 (also not shown in FIG. 1B or 1C). FIGS. 1B and 1C also illustrate the reference electrode 140 positioned outside of the recipient's cochlea and a portion of the reference lead region 142.

As described further below, the electrode devices 128(1)-128(22) each comprise, among other elements, a hermetically sealed integrated circuit (IC) 154 and a stimulation electrode 160 via which electrical (current) stimulation signals may be sourced (i.e., delivered) to, or sunk (i.e., received) from, a recipient's tissue. The electrode devices 128(1)-128(22) are all connected to the stimulator unit 120 via the same single wire 146 and the electrode devices 128(1)-128(22) are each individually addressable via this single wire 146. The electrode devices 128(1)-128(22) and the single wire 146 collectively form a single-wire (one-wire) electrode array 126. That is, stimulating assembly 118 includes a single-wire electrode array 126 via which stimulating signals can be delivered to a recipient. In operation, only the electrode 160 of each electrode device 128(1)-128(22) is in electrical contact with the recipient's body tissue/fluid, while other parts of the electrode devices 128(1)-128(22), and more generally the cochlear implant 104, are insulated from the recipient's body tissue/fluid by, for example, ceramic or titanium encapsulations, an insulating elastomer (e.g., silicone rubber), etc.

FIGS. 1A-1C illustrate an arrangement in which the cochlear implant system 100 includes an external component. However, it is to be appreciated that embodiments of the present invention may be implemented in cochlear implant systems, or other prosthesis systems, having alternative arrangements. For example, embodiments of the present invention can also be implemented in a totally implantable cochlear implant system, or another type of totally implantable tissue-stimulating prosthesis. In a totally implantable prosthesis, all components are configured to be implanted under skin/tissue of a recipient and, as such, the prosthesis operates for at least a finite period of time without the need of an external device.

FIG. 2 is a schematic diagram illustrating further details of an example electrode device 128 in accordance with embodiments presented herein. The electrode device 128 comprises a housing 150 that is attached to a base 152. In this embodiment, the housing 150 is a metal housing and the base 152 is a ceramic base. Together, the housing 150 and the base 152 form a hermetically sealed enclosure in which an integrated circuit (IC) 154 is disposed. As described further below, the integrated circuit 154 includes a number of functional components that can be used to source stimulation current to, or sink stimulation current from, a recipient's tissue.

The integrated circuit 154 is electrically connected to the housing 150 via a bond wire 156. Additionally, the housing 150 is electrically connected to the single wire 146 via a bond 158. Disposed on an outer surface of the ceramic base 152 is the electrode 160, which is sometimes referred to herein as a contact or pad, formed from an electrically conductive material. The electrode 160 is electrically connected to the integrated circuit 154 via a feedthrough 162. In practice, the electrode device 128 and the single wire 146 are substantially encapsulated within the electrically-insulating body 144 of the stimulating assembly 118, with only the electrode 160 exposed to the recipient's tissue/fluid. That is, other parts of the electrode device 128 and the single wire 146 are insulated from the recipient's body tissue/fluid. Merely for ease of illustration, the body 144 of the stimulation assembly has been omitted from FIG. 2.

FIG. 2 illustrates the arrangement for only a single electrode device 128. As described elsewhere herein, a single-wire electrode array in accordance with embodiments presented herein, such as array 126 of FIGS. 1A and 1B, includes a plurality of these electrode devices 128 (e.g., electrode devices 128(1)-128(22)) that are all electrically connected to a stimulator unit 120 via the same single wire 146. In accordance with the embodiments presented herein, the single wire 146 is used to power and communicate with, and deliver stimulation via, any of the electrode devices 128 in an individually addressable manner. In other words, the tissue-stimulating prostheses in accordance with the embodiments presented herein are configured to deliver controlled current stimulation to a recipient using a single-wire electrode array comprised of a plurality of independent electrode devices all connected to a stimulator unit via only a single wire. The ability to deliver controlled current stimulation using a single-wire electrode array requires a design that addresses several unique engineering challenges and requires the two 'terminals' of the electrode device (146 and 160) to act both as the mechanism for delivering power to the electrode device, and, as the mechanism of delivering stimulation current to tissue via the electrode device.

Although the ability to deliver controlled current stimulation using a single-wire electrode array creates several challenges, the use of a single wire connection between a stimulator unit and a plurality of electrode devices also provides several advantages relative to designs that make use of two or more wires, which would otherwise be required. For example, since only a single wire is present, the single wire cannot short to any other wires, thereby eliminating the common failure mechanism of wire shorting. As a result, the single wire does not need to be carefully insulated to a high degree of reliability to guard against shorts to/from neighboring wires. Additionally, a single wire can be easily connected to each electrode device without the need for multiple bonding sites at each electrode site. For example, in the example design described above in FIG. 2, the connection site on the electrode device comprises the metal housing of the integrated circuit enclosure. Although this design may be advantageous in certain arrangements, other designs may be used in accordance with embodiments presented herein.

As such, it is to be appreciated that the arrangement of FIG. 2 is merely an example implementation. Electrode devices in accordance with embodiments presented herein may have other arrangements where two electrical contacts (one connected to a single-wire and one in contact with the recipient's body) are isolated from one another and both have connections to an electronic circuit which is hermetically encapsulated. Other implementation may include, for example, an arrangement that uses two feedthroughs (or one as shown in FIG. 2), an arrangement in which the electronics are formed by a micro-assembly or are fully integrated, an arrangement in which ceramic forms part of the encapsulation, an arrangement in which a bond wire or some other elements is used for making electrical connections, etc.

Another advantage of a single-wire electrode array is a reduction in fabrication complexity relative to a multiple wire array. For example, the single wire could be combined with any metallic stiffening or structural members used in the design of the electrode array, which is not possible if a multiple wire interface is used. Moreover, a single-wire electrode array may be made thinner (i.e., with a smaller cross-sectional area) than a conventional multiple wire array since less cross-sectional area is needed to accommodate connecting wires extending from the electrodes to the stimulator unit.

Figure 3:
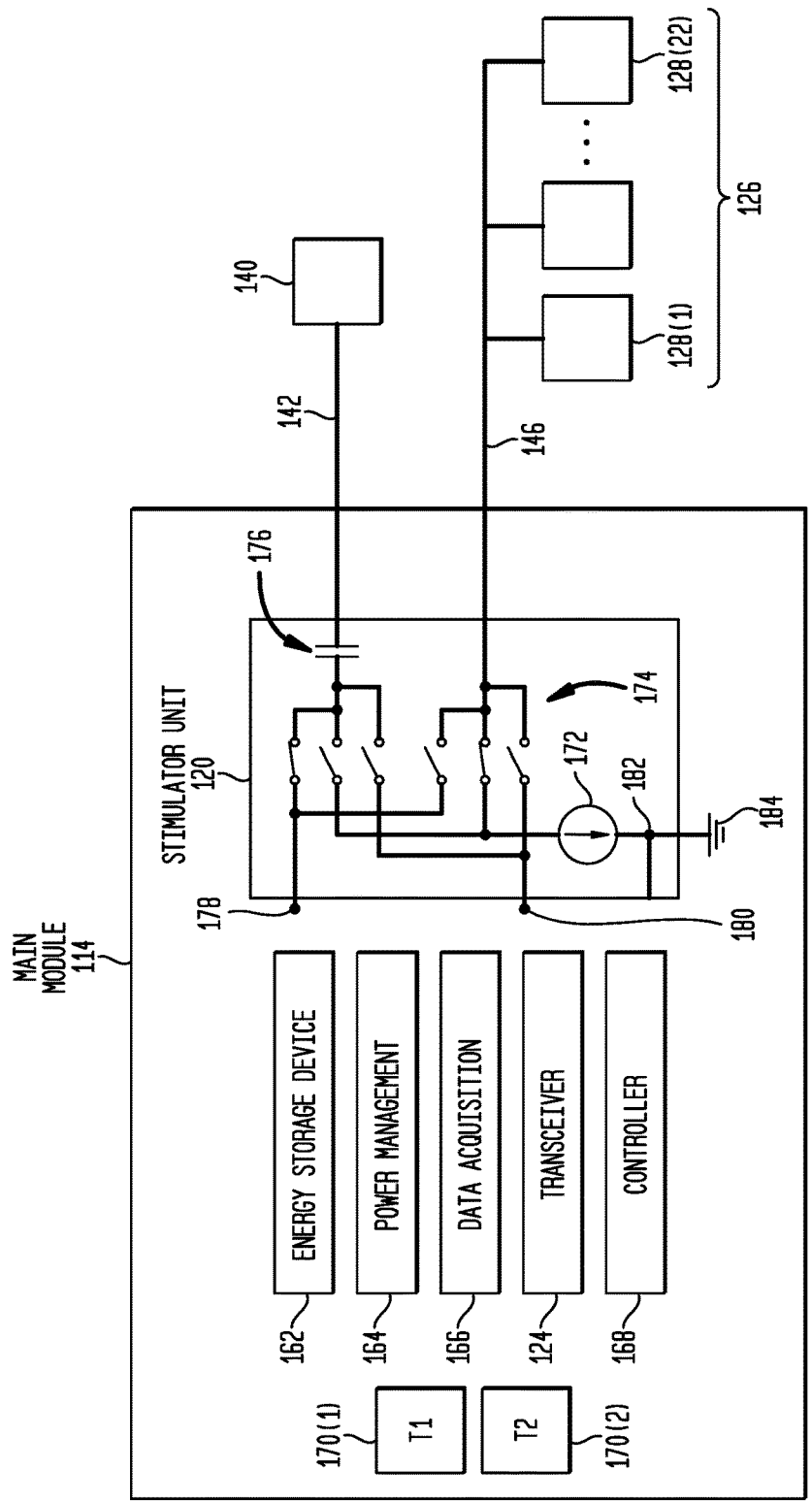
FIG. 3 is a block diagram illustrating a main module and a single-wire electrode array in accordance with embodiments presented herein.

FIG. 3 is schematic block diagram illustrating further details of the main module 114 in accordance with embodiments presented herein. As shown, the main module 114 includes an energy storage device 162 (e.g., an implanted battery or a short-term energy storing capacitor), a power management unit 164, a data acquisition unit 166, the transceiver unit 124, a controller 168, and the stimulator unit 120.

The power management unit 164 is configured to supply, using the energy storage device 162, a suitable stimulation power (VDD) to the stimulator unit 120. As noted above, the transceiver 124 is configured to enable communication with other parts of the cochlear implant system 100 (e.g., via a transcutaneous link attached to ports 170(1) and 170(2)). The data acquisition unit 166 is configured to acquire data, such as electrode voltages, neural response signals, implant health and diagnostic signals, etc. The controller (control unit) 168 is configured to control the operations of the various other components of the main module 114. For ease of illustration, connections between the various components of the main module 114 have been omitted from FIG. 3

As noted, the main module 114 also comprises the stimulator unit 120. FIG. 3 illustrates an example arrangement for stimulator unit 120, but it is to be understood by a person skilled in the art that stimulator units in accordance with embodiments presented herein may use other arrangements. In specific illustrative arrangement of FIG. 3, the stimulator unit 120 comprises a current source 172 which can be directed to either the one-wire electrode array 126 (i.e., electrically connected to the single wire 146) or to the reference electrode 140 (i.e., electrically connected to the reference lead 142) using a switch network 174.

The switch network 174 comprises a plurality of switches implemented, for example, using metal-oxide-semiconductor (MOS) transistors on an integrated circuit. The switch network 174 has a pin/node 178 for receiving VDD and a pin/node 180 for receiving data that can be provided to the electrode devices 128 via the single wire 146. In other words, node 180 is connected to a signal/data wire (not shown in FIG. 3) from the controller 168. The switch network 174 also has a node 182 connected to a ground 184. As shown, a capacitor 176 may be placed in series with the reference electrode 140 as is the practice in some stimulator designs (principally to eliminate the flow of DC in that electrode). A similar capacitor may also be placed in series with the single wire 146 although this is not show in any figures. Similar capacitors may also be placed in series with electrode contact 160 within some or all of the electrode units, again principally to eliminate DC through the electrode contact 160.

The stimulator unit 120 operates in three primary operational modes, namely (1) sourcing current via one or more of the electrode devices 128, (2) sinking current at one or more of the electrode devices 128, where the current is sourced via the reference electrode 140, or (3) providing power and/or data on the single wire 146. The switch network 174 operates, in essence, as a mechanism for connecting one of three terminals (VDD, data, or the current source) to the single wire 146 or the reference lead 142, thereby selectively enabling the various operation modes of the stimulator unit 120.

Figure 4:
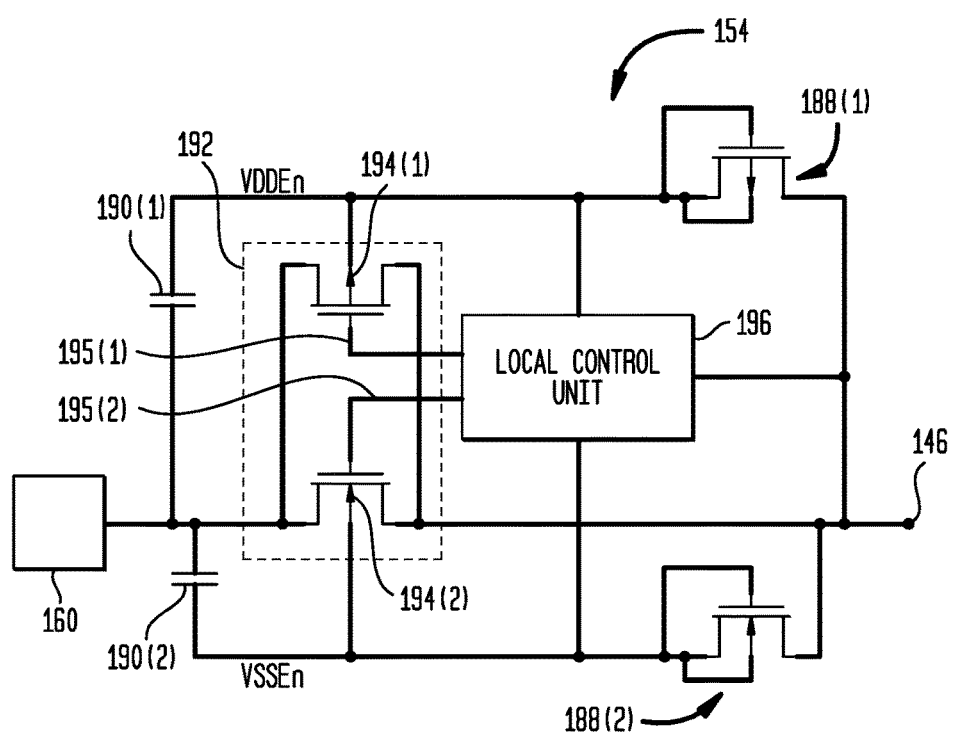
FIG. 4 is a schematic diagram illustrating one arrangement for an integrated circuit of an electrode device in accordance with embodiments presented herein.

FIG. 4 is a schematic diagram illustrating the details of an example integrated circuit 154 forming part of an electrode device 128 in accordance with embodiments presented herein. As shown, the integrated circuit 154 is connected between the single wire 146 and the electrode 160, each of which is schematically represented in FIG. 4 by a corresponding block. Also for ease of illustration various connections and other components of the electrode device 128 (e.g., the housing 150, bond 158, bond wire 156, base 152, feedthrough 162, etc.) have also been omitted from FIG. 4.

In the specific example of FIG. 4, the integrated circuit 154 includes two rectifying elements 188(1) and 188(2) (e.g., transistors configured as diodes in opposite polarity) that are used to direct current received on the single wire 146 to the two local supply capacitors 190(1) and 190(2). The voltages on these capacitors 190(1) and 190(2), with respect to the voltage on the electrode 160, are referred to herein as VDDEn (positive) and VSSEn (negative). The voltages VDDEn and VSSEn are the local power supplies for the integrated circuit electronics. For example, when it is desired that the electrode device 128 participates in stimulation, the electrode switch 192, which is comprised of transistors 194(1) and 194(2), is turned on (closed, low impedance) allowing the stimulator unit 120 in the main module 114 to pass current in either direction through the corresponding electrode device 128. The electrode switch 192 may also be turned on (low impedance) if the particular electrode device 128 participates in other actions such as post-stimulation shorting or measurements involving that electrode device. If the electrode device 128 does not participate in any actions, then the electrode switch 192 will be turned off (high impedance). The state of the electrode state 192 is controlled by a local control unit 196 which is configured to decode data sent from the stimulator unit 120 via the single wire 146. In operation, the local power supplies (i.e., capacitors 190(1) and 190(2)) have sufficient storage capacity to keep the electrode switch 192 in the off state even when there are considerable voltage differences between the single wire 146 and the electrode 160 as a result of, for example, stimulation on other electrode devices.

In an example operation of FIG. 4, the main module 114 delivers a "wake-up" or "initialization" signal on the single wire 146. This initialization signal, which may comprise one or more pulses, is received at each of the electrode devices 128 connected to the single wire 146. This initialization signal is configured to charge the capacitors 190(1) and 190(2) and, accordingly, power-up the local control units 196 in all of the electrode devices 128.

After sending the initialization signal, the main module 114 sends an encoded data signal on the single wire 146. The data signal is encoded with an address, code, identifier, etc. (collectively and generally referred to herein as "identifier") associated with one of the connected electrode devices. More specifically, each electrode device 128 in a single wire array has an associated identifier with which data can be selectively encoded by the controller 168 in the main module 114. When the controller 168 sends an encoded data signal, all of the electrode devices 128 connected to the single wire 146 will receive the encoded data signal. Additionally, since the local control units 196 are all powered up (due to the initialization signal), the data signal will be decoded by each of the local control units. However, a local control unit 128 will only act on the encoded data signal when the data signal is encoded with its associated identifier. In other words, the local control units 196 are configured to ignore data signals that are not encoded with an identifier for the specific electrode device.

The controller 168 is aware of the unique identifiers associated with electrode device 128. Therefore, when the controller 168 needs to communicate with a specific electrode device 128 connected to the single wire 146, the controller 168 sends a data signal that is encoded with the identifier for the specific electrode device 128. In addition to the identifier, this data signal also includes instructions for execution by the local control unit 196.

In summary, the electrode devices 128 connected to the single wire 146 are individually addressable using a unique code where each electrode device has its own decoder (local control unit 196) that will only act upon commands that are tagged with its associated unique code. In one embodiment, a data signal tells the electrode device 128 to close or open its electrode switch 192 for a period of time (e.g., the next X milliseconds). In other embodiments, the data signal can provide other information to the local control unit 196.

When delivering power, an alternating/fluctuating (e.g., AC) voltage is applied between terminal 146 and 160 of an electrode device 128 so that capacitors 190(1) and 190(2) within the electrode device charge up and keep the electronics (e.g., local control unit 196 and switch 192) of the electrode device powered for sufficient time. When acting to deliver current, the electrode device 128 configures itself (upon receiving instruction from the controller 168) into a low impedance mode where current supplied from stimulator unit 120 flows between terminals 146 and 160 via the transistors 194(1) and 194(2), which are now configured to be low impedance by the local control unit 196. Shown in FIG. 4 are control lines 195(1) and 195(2) which connect the gates of transistors 194(1) and 194(2), respectively, to the local control unit 196. The voltage of these control lines 195(1) and 195(2), driven by the local control unit 196, are what determines whether the transistors 194(1) and 194(2) are in a low or high impedance state.

Figure 5:
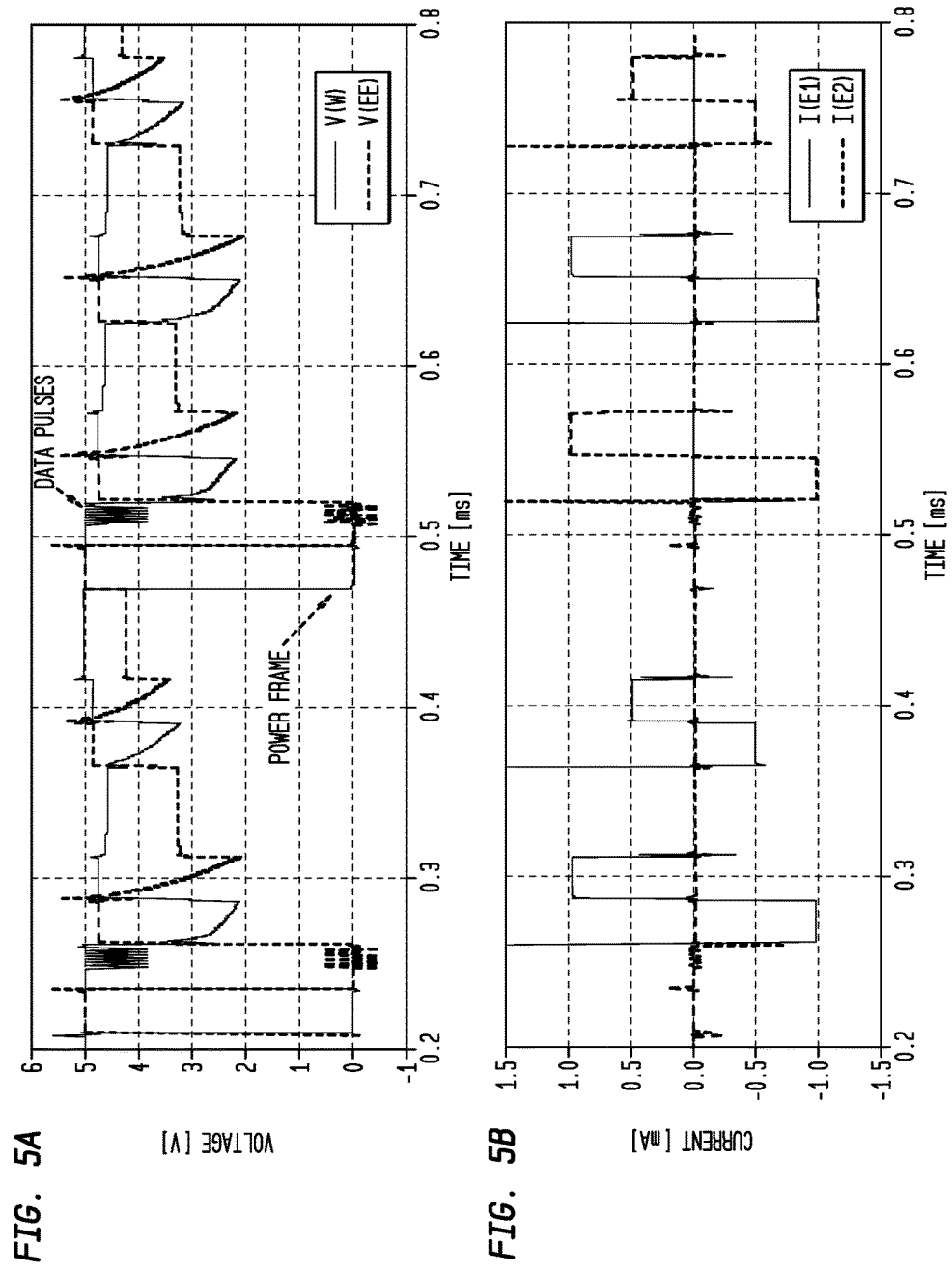
FIG. 5A is a diagram illustrating example voltages during operation of a single-wire electrode array in accordance with embodiments presented herein.
FIG. 5B is a diagram illustrating example currents during operation of a single-wire electrode array in accordance with embodiments presented herein.

FIGS. 5A and 5B are graphs illustrating example interface voltages and electrode currents, respectively, during stimulation using a one-wire electrode array in accordance with embodiments presented herein. For ease of illustration, FIGS. 5A and 5B share a common time scale.

When the electrode switches 192 in all electrode devices 128 are left in an open circuit state (which is also the start-up condition), an alternating current (AC) voltage between the single wire 146 and the reference electrode 140 will activate the power rectifiers in all electrode devices 128, enabling these to subsequently participate in stimulation. In this state, data can also be transmitted to the electrode devices 128, as detailed above, to communicate the need for them to participate in upcoming stimulation events. This can be seen in FIG. 5A, which shows the voltages on the single wire interface, referenced as V(W) and the voltage on the reference electrode, denoted as V(EE) during power frames and data pulses forming an encoded data signal. Both voltages V(W) and V(EE) in FIG. 5A are show with respect to the internal ground voltage of the controller unit 144. FIG. 5B illustrates the current flowing through the terminals 146 and 160 of two example electrode devices 128(1), denoted in FIG. 5B as E1, and 128(2), denoted in FIG. 5B as E2, when power and data is transmitted in accordance with FIG. 5A. FIG. 5A and FIG. 5B depict five complete biphasic pulse cycles of stimulation delivery. In the first biphasic pulse cycle −1.0 mA is delivered through electrode device E1 in phase 1 and +1.0 mA is delivered through device E1 in phase 2. In the second biphasic cycle −0.5 mA is delivered through E1 in phase 1 and +0.5 mA through E1 in phase 2. In the third biphasic cycle −1.0 mA is delivered through electrode device E2 in phase 1 and +1.0 mA is delivered through device E2 in phase 2. In the fourth biphasic pulse cycle −1.0 mA is delivered through device E1 in phase 1 and +1.0 mA is delivered through device E1 in phase 2. In the fifth biphasic pulse cycle −0.5 mA is delivered through device E2 in phase 1 and +0.5 mA is delivered through device E2 in phase 2.

In accordance with embodiments presented herein, all current flowing into (out of) the single-wire 146 wire will return out of (into) the wire running through lead region 142. That is, the currents flow as "monopolar" currents in the cochlea. This is also the case for the currents in the power frames and in the data frames (as can be seen in FIG. 5B). These currents, therefore, have to be managed in such a way that they are below perception threshold and that they are fluctuating (e.g., AC) in nature. As would be appreciated by a person skilled in the art, these features are enabled by the arrangements described herein.

Figure 6:
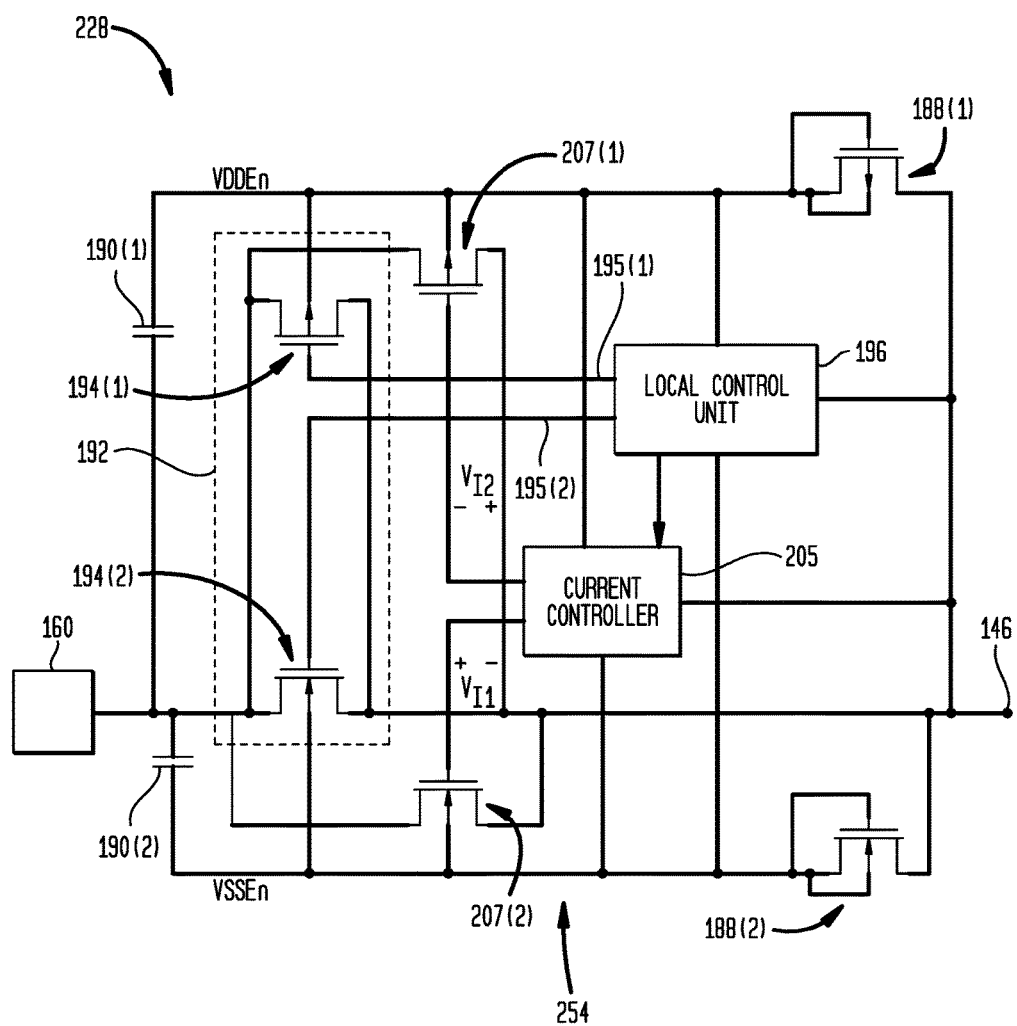
FIG. 6 is a schematic diagram illustrating another arrangement for an integrated circuit of an electrode device in accordance with embodiments presented herein.

FIG. 6 is a schematic diagram illustrating an alternative arrangement for an integrated circuit, referred to as integrated circuit 254, of an electrode device 228 in accordance with embodiments presented herein. In the embodiment of FIG. 6, the integrated circuit 254 is connected between the single wire 146 and an electrode 160 and comprises several of the same elements described above in FIG. 4, including the rectifying elements 188(1) and 188(2), the local supply capacitors 190(1) and 190(2), the electrode switch 192, and the local control unit 196. However, the integrated circuit 254 also includes a current controller 205 and two configurable current sources 207(1) and 207(2). In general, the integrated circuit 254 is configured to allow for a controlled fraction of the current delivered on the single wire 146 by the main module 114 so that current can be directed through several electrode devices simultaneously in the same direction.

For example, in one implementation multiple electrode devices, referred to as electrode devices E1, E2, E3, and E4 each have the arrangement shown in FIG. 6. In this example, the current source 172 (FIG. 3) in the stimulator unit 120 is set to draw 1 mA of current and electrode device E3 is set active by closing its electrode switch 192 (closing transistors 194(1) and 194(2)). The current sources 207(2) in each of electrode devices E2 and E4 are set to draw 0.2 mA (i.e., each operating as current sinks) and, as such, 0.6 mA remains to flow through electrode device E3. The current controllers 205 in E2 and E4, each of which operate with a specified current, control the gate-source voltage ($V_{I1}$) of the current source 207(2) and the source-gate voltage ($V_{I2}$) of the current source 207(1), such that each current source conducts the desired amount of current. Since the total current flowing through the single wire 146 is set by the current source 172 in the main module 114, the direction of the current flow in all electrode devices E2, E3, and E4 is the same. In the current controlled electrode devices, the corresponding current source 207(1) is activated when the direction of the current is from the single wire 146 to the electrode 160, while the corresponding current source 207(2) is activated when the direction of the current is from the electrode 160 to the single wire 146. It is to be appreciated that the single transistor current sources (i.e., current sources 207(1) and 207(2) in FIG. 6) may be replaced with other types of digitally controlled stimulating current source circuits or, in other arrangements, could be combined with the transistors 194(1) and 194(2) forming electrode switch 192.

In summary, FIG. 6 illustrates an arrangement in which the electrode switches 192 in one or more electrode devices 129 are current limited, in a controllable manner, such that current can flow in a number of electrode devices simultaneously.

Figure 7:
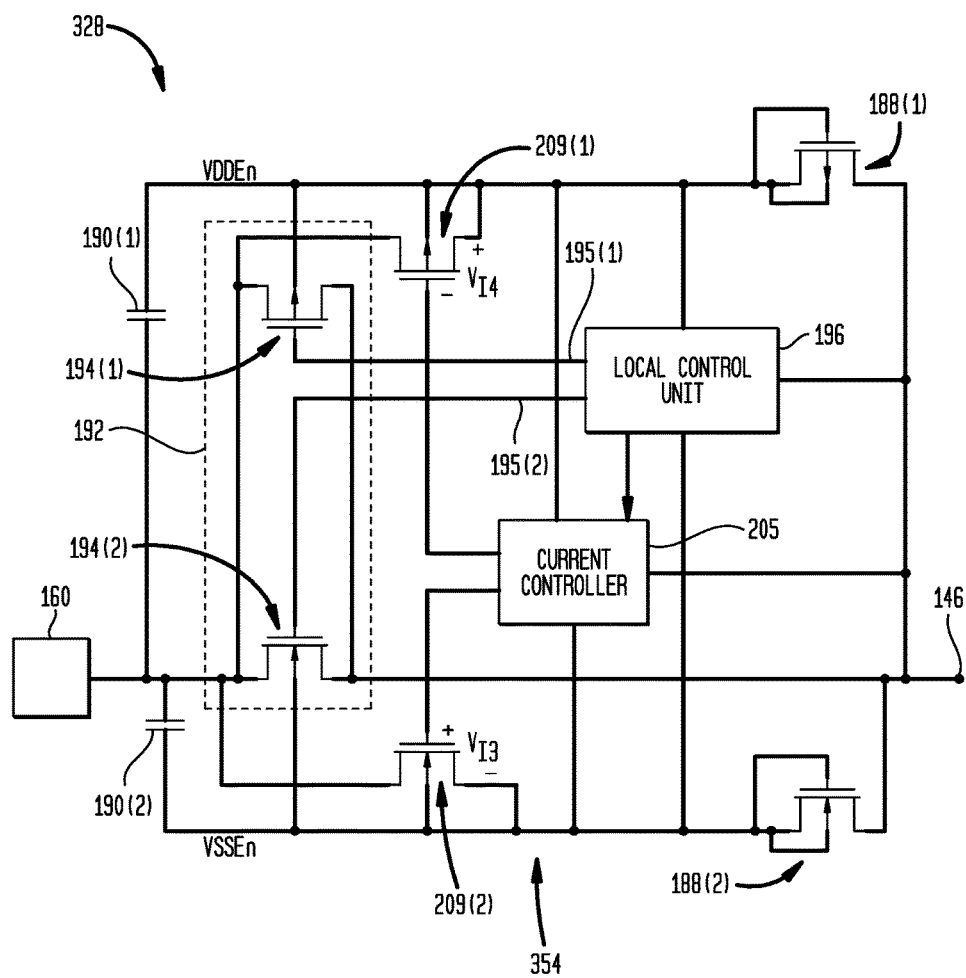
FIG. 7 is a schematic diagram illustrating another arrangement for an integrated circuit of an electrode device in accordance with embodiments presented herein.

FIG. 7 is a schematic diagram illustrating a further arrangement for an integrated circuit, referred to as integrated circuit 354, of an electrode device 328 in accordance with embodiments presented herein. In the embodiment of FIG. 7, the integrated circuit 354 is connected between the single wire 146 and an electrode 160 and comprises several of the same elements described above in FIG. 6, including the rectifying elements 188(1) and 188(2), the local supply capacitors 190(1) and 190(2), the electrode switch 192, the local control unit 196, and the current controller 205. Also similar to the arrangement of FIG. 6, the integrated circuit 354 is configured to allow for a controlled fraction of the current delivered on the single wire 146 by the main module 114 to be directed through several electrode devices simultaneously in the same direction. However, the arrangement of FIG. 7 also enables current to flow through one or more other electrode devices in an opposite direction.

In the embodiment of FIG. 7, the integrated circuit 354 includes current sources 209(1) and 209(2) that have their source terminals connected to the local power supplies VDDEn and VSSEn, respectively, and the current controller 205 operates to control the gate-source voltage ($V_{I3}$) of current source 209(2) and the source-gate voltage ($V_{I4}$) of current source 209(1) to set their respective currents. The advantage of this arrangement is that the direction of the current flow in a current controlled electrode device 328 may be opposite of that of another electrode device 328 that directs the single wire current by closing its corresponding electrode switch 192. Such opposite current flow may allow for refined control of the current flowing in the excitable tissue and may also allow for the use of intracochlear stimulation modes, such as bipolar mode, where current is sourced from one intracochlear electrode device and sunk into another intracochlear electrode device simultaneously. If the current flow direction in an electrode device 328 is opposite that of a primary electrode device 328 (i.e., the electrode device that directs the single wire current by closing its corresponding electrode switch 192), then the supply capacitors 190(1) or 190(2) will be partially discharged by the electrode current and would have to be recharged after the stimulation event. In other words, the opposite stimulation current is delivered from the stored charge in the supply capacitors 190(1) or 190(2).

In summary, FIG. 7 illustrates an arrangement in which the capacitors 190(1) and 190(2) can be used to deliver/take stimulation current (and hence be partially depleted). As such, current may flow in one direction in a primary/main electrode device, and in opposite directions in one or more auxiliary electrode devices simultaneously if desired. As such, the arrangement of FIG. 7 is able to delivery phased-array and other intracochlear stimulation modes using a single wire connection between a stimulator unit and a plurality of electrode devices.

Figure 8:
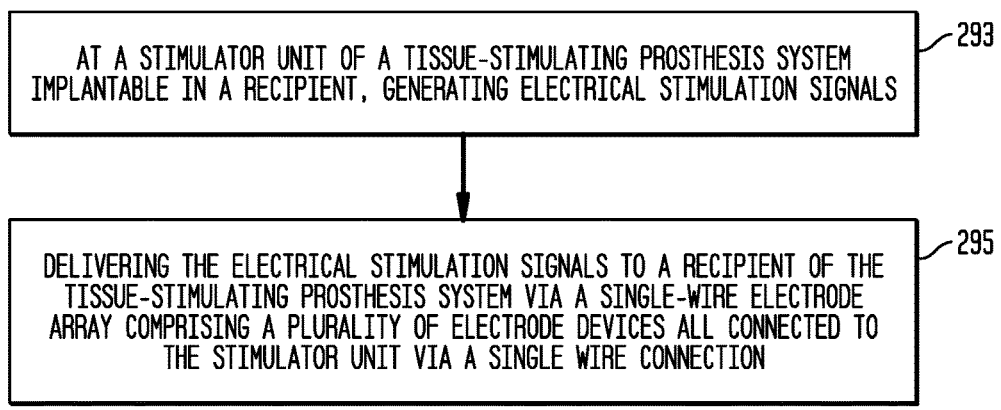
FIG. 8 is a flowchart of a method in accordance with embodiments presented herein.

FIG. 8 is flowchart of a method 291 in accordance with embodiments presented herein. Method 291 begins at 293 where a stimulator unit of a tissue-stimulating prosthesis system implantable in a recipient generates electrical stimulation signals. At 295, the electrical stimulation signals are delivered to a recipient of the tissue-stimulating prosthesis system via a single-wire electrode array comprising a plurality of electrode devices all connected to the stimulator unit via a single wire connection.

In certain examples, the tissue-stimulating prosthesis system comprises a hearing prosthesis, such as a cochlear implant, and the method 291 further comprises receiving sound signals at one or more sound input elements of the tissue-stimulating prosthesis system, and processing the sound signal to generate control signals representative of the sound signals. In these examples, the stimulator unit is configured to generate the electrical stimulation signals based on the control signals.

Merely for ease of illustration, the embodiments presented herein are primarily described herein with reference to one type of tissue-stimulating prosthesis, namely a cochlear implant. However, it is to be appreciated that the techniques presented herein may be used with other tissue-stimulating prostheses including, for example, auditory brainstem stimulators, implantable pacemakers, defibrillators, functional electrical stimulation devices, pain relief stimulators, visual prostheses, other neural or neuromuscular stimulators, etc. in these arrangements, the main module or the single-wire electrode array have been different physical or electrical arrangements than that shown and described above. For example, in the case of a planar electrode array used for a retinal implant, the single "wire" could comprise a thin metallic mesh or net-like structure spread over the non electrode side of the array and connected to each "smart" electrode on the side away from the electrode pad.

It is to be appreciated that the above embodiments are not mutually exclusive and may be combined with one another in various arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A tissue-stimulating prosthesis system, comprising:
   a stimulator unit configured to generate, based on one or more processed signals, electrical stimulation signals for delivery to a recipient; and
   a single conductive connection;
   a single-wire electrode array comprising a plurality of electrode devices all electrically connected to the stimulator unit via only the single conductive connection,
   wherein each of a plurality of the electrode devices comprises a configurable current source, and wherein each of the plurality of the electrode devices are individually addressable by the stimulator unit via the single conductive connection for delivery of the electrical stimulation signals to the recipient using commands encoded with a unique code set for each of the electrode devices.

2. The tissue-stimulating prosthesis system of claim 1, wherein the electrode devices are powered via power signals received via the single conductive connection.

3. The tissue-stimulating prosthesis system of claim 2, wherein each of the electrode devices comprises a local control unit that will only act upon commands that are tagged with the unique code associated with the corresponding electrode device.

4. The tissue-stimulating prosthesis system of claim 2, wherein each of the electrode devices comprises an electrode switch configured to permit current to flow through the associated electrode device from the single conductive connection to tissue of the recipient, and wherein the commands include timing information indicating when an electrode switch should be opened to permit current flow.

5. The tissue-stimulating prosthesis system of claim 1, wherein the stimulator unit is configured to simultaneously deliver the electrical stimulation signals to the recipient via the single conductive connection and two or more of the electrode devices.

6. The tissue-stimulating prosthesis system of claim 5, wherein each of the plurality of the electrode devices comprises at least two configurable current sources and a current controller such that a controlled fraction of the electrical stimulation signals received via the single conductive connection can be directed through the two or more of the electrode devices simultaneously in the same direction.

7. The tissue-stimulating prosthesis system of claim 1, wherein the stimulator unit is configured to simultaneously deliver the electrical stimulation signals to the recipient via the single conductive connection and two or more of the electrode devices such that current flows through a first of the two or more electrode devices in a first direction and current flows through a second one of the two or more electrode devices in a second direction, wherein the second direction is a current flow direction that is opposite to the first direction.

8. The tissue-stimulating prosthesis system of claim 1, further comprising:
   one or more sound input elements configured to receive sound signals; and
   a sound processor configured to generate one or more processed signals representative of the sound signals,
   wherein the stimulator unit is configured to generate the electrical stimulation signals based on at least one of the one or more processed signals, and wherein the electrical stimulation signals are configured to evoke perception of the sound signals by the recipient.

9. The tissue-stimulating prosthesis system of claim 8, wherein the tissue-stimulating prosthesis is a cochlear implant.

10. A tissue-stimulating prosthesis system, comprising:
    a plurality of electrode devices configured to be implanted in a recipient;
    a stimulator unit configured to generate electrical stimulation signals for delivery to the recipient; and
    only a single conductive path electrically connecting all of the electrode devices to the stimulator unit,
    wherein each of a plurality of the electrode devices comprises a configurable current source, and wherein each of the plurality of the electrode devices are individually addressable by the stimulator unit via the single conductive path for delivery of the electrical stimulation signals to the recipient, and wherein the plurality of electrode devices are each powered via power signals received via the single conductive path.

11. The tissue-stimulating prosthesis system of claim 10, wherein each of the plurality of electrode devices includes an electrode switch to enable current to flow from the single conductive path to tissue of the recipient via the respective electrode device, and wherein the electrode switch in a respective electrode device is activated to permit current flow based on encoded data signals received at the respective electrode switch via the single conductive path.

12. The tissue-stimulating prosthesis system of claim 10, wherein each of the electrode devices comprises a local control unit that will only act upon commands that are tagged with the unique code associated with the corresponding electrode device.

13. The tissue-stimulating prosthesis system of claim 10, wherein each of the electrode devices comprises an electrode switch configured to permit current to flow from the single conductive path to tissue of the recipient through the associated electrode device, and wherein the commands include timing information indicating when an electrode switch should be opened to permit current flow.

14. The tissue-stimulating prosthesis system of claim 10, wherein the stimulator unit is configured to simultaneously deliver the electrical stimulation signals to the recipient via the single conductive path and two or more of the electrode devices.

15. The tissue-stimulating prosthesis system of claim 14, wherein each of the plurality of the electrode devices comprises at least two configurable current sources and a current controller such that a controlled fraction of the electrical stimulation signals received via the single conductive path can be directed through the two or more of the electrode devices simultaneously in the same direction.

16. The tissue-stimulating prosthesis system of claim 10, wherein the stimulator unit is configured to simultaneously deliver the electrical stimulation signals received via the single conductive path to the recipient via two or more of the electrode devices such that current flows through a first of the two or more electrode devices in a first direction and current flows through a second one of the two or more electrode devices in a second direction, wherein the second direction is a current flow direction that is opposite to the first direction.

17. A method performed in a tissue-stimulating prosthesis system comprising a stimulator unit and an electrode array comprising a plurality of electrode devices electrically connected to the stimulator unit via only a single conductive connection, and wherein each of a plurality of the electrode devices comprises a configurable current source, the method comprising:
at the stimulator unit, generating electrical stimulation signals;
individually addressing, via the single conductive connection, at least one of the plurality of electrode device using commands encoded with a unique code set for the least one of the plurality of electrode devices; and
delivering the electrical stimulation signals to a recipient of the tissue-stimulating prosthesis system via only the single conductive connection and the least one of the configurable current sources of the plurality of the electrode devices.

18. The method of claim 17, wherein delivering the electrical stimulation signals to the recipient via only the single conductive connection and the least one of the plurality of electrode devices comprises:
simultaneously delivering the electrical stimulation signals via the single conductive connection and two or more of the plurality of electrode devices, wherein the electrical stimulation signals have the same polarity at each of the two or more electrode devices.

19. The method of claim 18, wherein delivering the electrical stimulation signals to the recipient via only the single conductive connection and the least one of the plurality of electrode devices comprises:
simultaneously delivering the electrical stimulation signals to the recipient via the single conductive connection and two or more of the plurality of electrode devices such that current flows through a first of the two or more electrode devices in a first direction and current flows through a second one of the two or more electrode devices in a second direction, wherein the second direction is a current flow direction that is opposite to the first direction.

20. The method of claim 17, comprising:
receiving sound signals at one or more sound input elements of the tissue-stimulating prosthesis system; and
processing the sound signal to generate control signals representative of the sound signals,
wherein the stimulator unit is configured to generate the electrical stimulation signals based on the control signals.

* * * * *